US008979938B2

(12) United States Patent
Linares

(10) Patent No.: US 8,979,938 B2

(45) Date of Patent: Mar. 17, 2015

(54) ARTIFICIAL KNEE IMPLANT INCLUDING LIQUID BALLAST SUPPORTING / ROTATING SURFACES AND INCORPORATING FLEXIBLE MULTI-MATERIAL AND NATURAL LUBRICANT RETAINING MATRIX APPLIED TO A JOINT SURFACE

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 799 days.

(21) Appl. No.: 12/266,695

(22) Filed: Nov. 7, 2008

(65) Prior Publication Data

US 2009/0125108 A1 May 14, 2009

Related U.S. Application Data

(60) Provisional application No. 60/986,486, filed on Nov. 8, 2007.

(51) Int. Cl.

| | |
|---|---|
| ***A61F 2/32*** | (2006.01) |
| ***A61F 2/38*** | (2006.01) |
| *A61F 2/08* | (2006.01) |
| *A61F 2/30* | (2006.01) |

(52) U.S. Cl.

CPC ... *A61F 2/38* (2013.01); *A61F 2/08* (2013.01); *A61F 2/30965* (2013.01); *A61F 2002/30673* (2013.01); *A61F 2002/30934* (2013.01); *A61F 2002/30971* (2013.01)

USPC .................. 623/22.15; 623/14.12; 623/18.11; 623/19.12; 623/20.22

(58) Field of Classification Search

CPC ...... A61F 2/32; A61F 2/34; A61F 2002/3208

USPC .......... 623/14.12, 18.11, 20.14, 20.17, 22.11, 623/23.39, 20.4, 20.41, 22.15, 22.17, 22.21, 623/19.12, 20.22, 20.23, 20.28, 22.24, 623/21.13, 21.16, 23.4

See application file for complete search history.

(56) References Cited

U.S. PATENT DOCUMENTS

| | | | |
|---|---|---|---|
| 2,667,644 | A | 2/1954 | Johnson |
| 3,651,521 | A | 3/1972 | Devas |
| 3,798,679 | A | 3/1974 | Ewald |
| 3,875,594 | A | 4/1975 | Swanson |
| 3,964,106 | A | 6/1976 | Hutter, Jr. et al. |

(Continued)

FOREIGN PATENT DOCUMENTS

| | | |
|---|---|---|
| JP | 07116184 A | 5/1995 |

*Primary Examiner* — Thomas J Sweet

*Assistant Examiner* — Seema Mathew

(74) *Attorney, Agent, or Firm* — Gifford, Krass, Sprinkle, Anderson & Citkowski, P.C.; Douglas J. McEvoy

(57) ABSTRACT

An artificial joint associated with an implant having a pair of three dimensional and structurally extending bones, each defining a contoured and opposing end face and collectively defining a joint location. A plasticized layer is applied to an end face of each bone and coacts in substantially frictional reducing fashion with an opposing end face of a further selected bone. The plasticized layer further includes at least a plurality of projecting contact locations, between which are defined a network of valleys for receiving, supporting, and distributing a lubricant across a surface area associated with the layer.

4 Claims, 5 Drawing Sheets

12 10 16 18 20 22 14

(56) References Cited

U.S. PATENT DOCUMENTS 4,055,862 A * 11/1977 Farling .................... 623/18.11
4,215,439 A 8/1980 Gold et al.
4,231,122 A 11/1980 Koeneman
4,328,593 A 5/1982 Sutter et al.
4,367,562 A 1/1983 Gauthier
4,538,305 A 9/1985 Engelbrecht et al.
4,714,477 A 12/1987 Fichera et al.
4,778,474 A * 10/1988 Homsy .................... 623/22.14
4,813,961 A * 3/1989 Sostegni .................... 623/23.39
4,950,298 A 8/1990 Gustilo et al.
4,964,868 A 10/1990 Bloebaum
4,990,161 A 2/1991 Kampner
5,007,934 A 4/1991 Stone
5,021,061 A 6/1991 Wevers et al.
5,092,898 A 3/1992 Bekki et al.
5,171,325 A 12/1992 Aulie
5,197,987 A * 3/1993 Koch et al. .................... 623/20.28
5,358,525 A * 10/1994 Fox et al. .................... 623/14.12
5,389,107 A 2/1995 Nassar et al.
5,462,362 A 10/1995 Yuhta et al.
5,480,448 A * 1/1996 Mikhail .................... 623/22.24
5,509,934 A 4/1996 Cohen
5,549,697 A * 8/1996 Caldarise .................... 623/22.26
5,549,699 A * 8/1996 MacMahon et al. ....... 623/22.21
5,549,700 A * 8/1996 Graham et al. ............ 623/22.14
5,553,476 A 9/1996 Oehy et al.
5,571,193 A 11/1996 Kampner
5,593,445 A 1/1997 Waits
5,641,323 A * 6/1997 Caldarise .................... 623/22.18
5,645,594 A * 7/1997 Devanathan et al. ...... 623/11.11
5,645,601 A * 7/1997 Pope et al. .................... 623/23.39
5,662,158 A 9/1997 Caldarise
5,676,702 A 10/1997 Ratron
5,702,476 A 12/1997 Limacher et al.
5,728,175 A 3/1998 Rincoe
5,800,566 A 9/1998 Gramnas
5,879,406 A 3/1999 Lilley
5,916,269 A * 6/1999 Serbousek et al. ......... 623/22.24
5,921,358 A 7/1999 Gramnas et al.
6,045,581 A * 4/2000 Burkinshaw ............... 623/18.11
6,129,765 A * 10/2000 Lopez et al. ............... 623/22.15
6,165,223 A 12/2000 Metzger et al.
6,258,126 B1 * 7/2001 Colleran .................... 623/20.29
6,290,727 B1 * 9/2001 Otto et al. .................... 623/22.21
6,368,354 B2 * 4/2002 Burstein et al. ............ 623/22.28
6,398,815 B1 6/2002 Pope et al.
6,530,956 B1 * 3/2003 Mansmann ................ 623/18.11
6,627,141 B2 9/2003 McNulty et al.
6,629,997 B2 * 10/2003 Mansmann ................ 623/14.12
6,645,251 B2 * 11/2003 Salehi et al. ............... 623/20.28
6,660,040 B2 12/2003 Chan et al.
6,682,567 B1 * 1/2004 Schroeder .................. 623/22.24
6,692,679 B1 2/2004 McNulty et al.
6,723,102 B2 4/2004 Johnson et al.
6,800,298 B1 10/2004 Burdick et al.
6,800,670 B2 10/2004 Shen et al.
6,811,568 B2 11/2004 Minamikawa
6,818,172 B2 11/2004 King et al.
6,866,685 B2 3/2005 Chan et al.
6,962,607 B2 11/2005 Gundlapalli et al.
7,044,983 B1 5/2006 Cheng et al.
7,066,958 B2 6/2006 Ferree
7,077,867 B1 * 7/2006 Pope et al. ................. 623/20.14
7,087,091 B1 8/2006 Chen et al.
7,109,181 B2 9/2006 Cowlen et al.
7,148,209 B2 12/2006 Hoemann et al.
7,175,666 B2 2/2007 Yao
7,179,298 B2 2/2007 Greenlee
7,186,364 B2 3/2007 King et al.
7,331,995 B2 2/2008 Eisermann et al.
7,384,430 B2 6/2008 Greer et al.
7,578,851 B2 8/2009 Dong et al.
7,771,485 B2 8/2010 Grundei
7,780,738 B2 8/2010 Khandkar et al.
7,803,193 B2 * 9/2010 Steinberg ................... 623/20.21
8,257,444 B2 * 9/2012 Linares ...................... 623/18.11
8,556,981 B2 * 10/2013 Jones et al. ................ 623/20.17
2002/0183845 A1 * 12/2002 Mansmann ................ 623/13.11
2003/0065401 A1 4/2003 Amrich et al.
2003/0114935 A1 * 6/2003 Chan et al. ................. 623/22.21
2003/0216669 A1 11/2003 Lang et al.
2004/0024460 A1 2/2004 Ferree
2004/0068322 A1 4/2004 Ferree
2005/0055100 A1 3/2005 Lewis et al.
2005/0149199 A1 * 7/2005 Steinberg ................... 623/22.23
2005/0171604 A1 8/2005 Michalow
2005/0192672 A1 9/2005 Wyss et al.
2005/0192674 A1 9/2005 Ferree
2005/0202371 A1 * 9/2005 McGuire .................... 433/201.1
2005/0287187 A1 12/2005 Mansmann
2006/0015186 A1 1/2006 Isaac
2006/0173542 A1 * 8/2006 Shikinami .................. 623/14.12
2007/0100450 A1 * 5/2007 Hodorek .................... 623/14.12
2007/0179613 A1 8/2007 Heinz
2007/0287027 A1 12/2007 Justin et al.
2008/0033567 A1 2/2008 Stchur
2008/0288081 A1 * 11/2008 Scrafton et al. ............ 623/20.33
2009/0076605 A1 3/2009 Linares
2009/0088846 A1 * 4/2009 Myung et al. .............. 623/14.12
2009/0125108 A1 5/2009 Linares
2010/0145451 A1 * 6/2010 Dee ............................ 623/14.12
2011/0066243 A1 * 3/2011 Rivin et al. ................ 623/14.12
2012/0209396 A1 * 8/2012 Myung et al. .............. 623/22.11
2013/0231750 A1 * 9/2013 Taylor ........................ 623/22.21

* cited by examiner 12
10
16
18
20
22
14

18
22
20
14

66
70
68
66
68
66
64

74
72
76
12
12

ARTIFICIAL KNEE IMPLANT INCLUDING LIQUID BALLAST SUPPORTING / ROTATING SURFACES AND INCORPORATING FLEXIBLE MULTI-MATERIAL AND NATURAL LUBRICANT RETAINING MATRIX APPLIED TO A JOINT SURFACE

CROSS-REFERENCE TO RELATED APPLICATIONS

This Application is a Non-Prov of Prov (35 USC 119(e)) application 60/986,486 filed on Nov. 8, 2007 and entitled ARTIFICIAL KNEE IMPLANT INCLUDING LIQUID BALLAST SUPPORTING/ROTATING SURFACES AND INCORPORATING A FLEXIBLE MULTI-MATERIAL AND NATURAL LUBRICANT RETAINING MATRIX APPLIED TO A JOINT SURFACE.

FIELD OF THE INVENTION

The present invention is an artificial implant for use with either real or artificial human bones. In particular, the implant of the present invention is an improvement over prior art implants, typically those constructed of a metallic or other synthetic material, in that it provides ballasting and frictionless support to opposing ends of first and second bones associated with such as a knee joint. In addition to providing support through the injection of ballasting fluid into a bladder defined between the bones, the present invention further provides a wide variety of additional structures for more effectively establishing cushioning and multi-directional support in the artificial joint area.

BACKGROUND OF THE INVENTION

The prior art is well documented with examples of artificial (or prosthetic) implant joints and related assemblies, the purpose for which being to replace an existing joint which has become worn through extended wear or irreplaceably damaged through disease or injury. One objective of such artificial joint implants, whether adapted for use with an existing bone remaining in the patient or as a component of one or more skeletal implants which includes a built-in joint, is in providing a desired amount of cushioning support. Examples of existing implant assemblies with built-in dampening means include, among others, the modular implant with micro-motion damper as set forth in U.S. Pat. No. 7,156,666, to Yao and the shock absorbent prosthetic hip joint of Nasser, U.S. Pat. No. 5,389,107. Additional references of note include the reduced-friction artificial joint set forth in Ferree 2004/0068322, as well as the composite prosthetic bearing in King U.S. Pat. No. 7,186,364.

SUMMARY OF THE INVENTION

The present invention discloses an artificial joint associated with an implant and having a pair of three dimensional and structurally extending bones, each defining a contoured and opposing end face and collectively defining a joint location. A plasticized layer, such as constructed of an antimicrobial plastic, is applied to an end face of each bone and, in use, coacts in substantially frictional reducing fashion with an opposing end face of a further selected bone. The plasticized layers each further include at least a plurality of projecting contact locations, between which are defined a network of valleys for receiving, supporting, and distributing a lubricant across a surface area associated with the layer.

Additional features include the plasticized layer exhibiting a polymeric based mat exhibiting a selected length, width and thickness for filling a three dimensional area associated with the joint location. The bones exhibit a hardened, e.g. typically composite, plastic terminating in a cartilage mimicking softened end plastic layer, the mat securing to a selected plastic layer and such that a plurality of ridges formed with the mat define the contact locations for an opposing softened plastic layer associated with the other of the bones.

The mat may also include a first additive selected from at least one of a carbon and a graphite, and a second additive selected from at least one of a ceramic and a metal for providing the flexible and polymeric based mat with enhanced wear resistant properties. The opposing bone structure may also establish a joint selected from a group including at least one of upper/lower knee joint and an outer/inner ball and socket joint. The contact location valleys established by the surface secured mat structure allow for the distribution of lubricant passageways, these being selected from any of linear, radial, and concentric shapes and which allow for the lubricant to be evenly distributed across the mat surfaces and thereby establishing a consistently lubricated and friction reducing profile along all opposing contact surfaces between the bones defining the selected joint region.

A related version of artificial joint associated with an implant can include a pair of three dimensional and structurally extending bones, each defining a contoured and opposing end face, and which collectively defines a joint location. In this version, a plurality of pockets are defined in a selected and exposed end face of one of the bones, the pockets being selected from at least one of rounded, arcuate, doughnut and cross shaped configurations.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Figure 1:
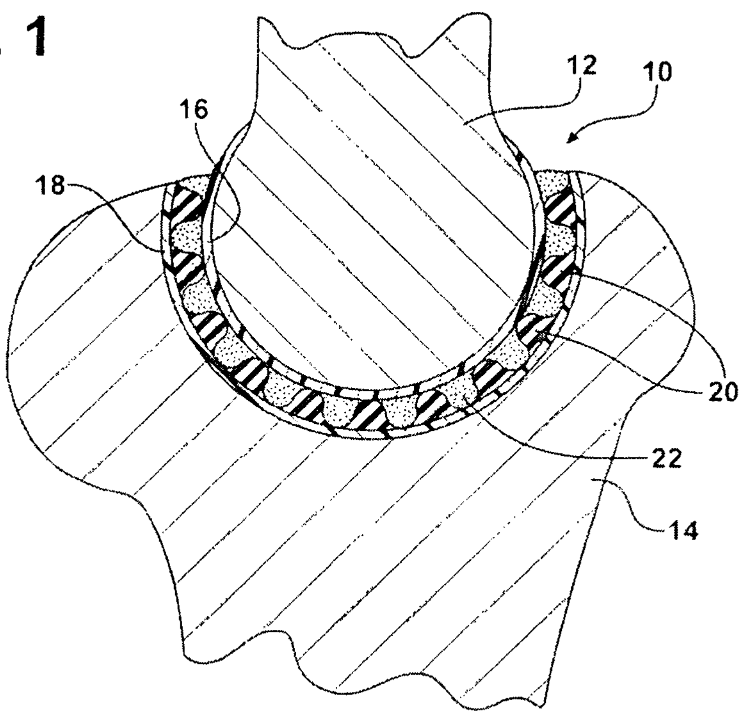
FIG. 1 is an illustration of an artificial knee implant according to a preferred embodiment of the present invention and exhibiting first (male) and second (receiver) bones, between which are disposed a rubberized and (self) lubricating mat configuration (such as ideally secured within an inner recess defining the second female bone) and further including an opposing surface mounted soft plastic liners associated with each of the hard plastic bones and, in cooperation with the mat configuration, establishing effortless contact with a second of the bones.

Referring now to FIG. 1, a first embodiment is illustrated at 10 of an artificial knee/joint implant according to the present inventions. As previously described, the skeletal implant is intended to operate as a replacement for human bone and joint structure (such as resulting from disease, accidents, etc.) and which is further an improvement over existing prosthetic metal implants and the like.

In particular the several embodiments of the present invention as described herein disclose a multi-material configured mat structure, this exhibiting such as a generally plastic/polymer based material exhibiting a generally planar and flexible/deformable construction, and into which is entrained smaller volumes (such as according to a graded particulate) of a graphite/carbon and a ceramic/metallic impregnate material. As will be further described, the construction of the flexible and joint located mat is such that it aggregates and evenly distributes across its surface area the natural lubricant fluids produced by the body. It is also envisioned that additional embodiments of the mat design can augment or (in certain instances) replace the natural fluid retention capabilities with a synthetic lubricant, and such as which can be introduced by external injection or internally provided secretion processes.

The knee and ligament embodiment featured at 10 exhibits first 12 and second 14 bones, these typically corresponding to a patient's upper and lower leg bones and which further define particularly configured and opposing/seating locations which is defined a joint region 16. As further understood, the bones 12 and 14 are typically artificial prostheses, these including such as plastic, metal or other suitable material constructions which exhibit the necessary properties of durability and resilience.

Referring again to FIG. 1, the implant generally referenced at 10 includes a first male bone 12 and a second female/receiver bone 14, and between which is disposed a rubberized and (self) lubricating mat configuration, such as in a preferred embodiment secured to an inner recess associated with the female bone 14. Each of the male 12 and receiver 14 bones are configured to mimic natural bone shaping for a given application and may be constructed from such as a hardened plastic.

Both the male and female joint defining and contacting surfaces further include a softened (cartilage replicating) plastic layer, see at 16 for male bone 12 and at 18 for receiver bone 14, and with the mat configuration, see at 20, being established therebetween. As will be described, the surface mounted soft plastic liners, associated with each of the hard plastic bones, and in cooperation with the lubricant inducing and distributing mat configuration, establishes substantially effortless contact along the joint location defined between the bones. As is also known, each of the plasticized layers, including the softened layers 16 and 18 as well as the mat configuration 20, may exhibit a specified shape and size and further can include such as an antimicrobial plastic.

Figure 2:
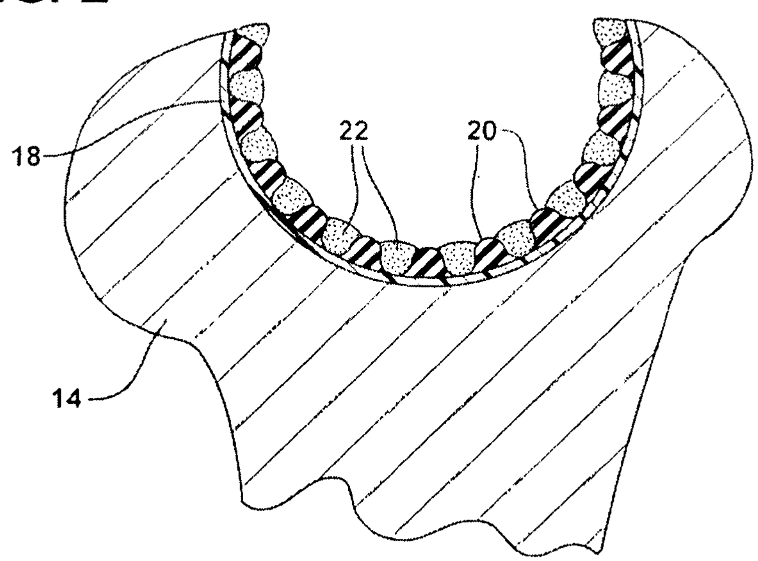
FIG. 2 is an enlarged illustration of a the receiver bone, and in particular showing the seepage inducing/self-lubricating mat consisting of such as three different intermixed materials inter-molded together and secured against the associated soft plastic liner, in turn sandwiched between the lubricating mat and the hardened, three dimensional plastic bone.

Referring to FIG. 2, an enlarged illustration is shown of the receiver bone 14 only, and in particular showing the seepage inducing/self-lubricating mat, at 20, and consisting of such as three different intermixed materials inter-molded together and secured against the associated soft plastic liner 18, in turn sandwiched between the lubricating mat and the hardened, three dimensional plastic receiver bone 14. As described previously, the matrix composition of the mat 20 combines a variety of materials, e.g. such as again including a polymer based matrix into which is intermixed or otherwise entrained such as through a stamping, molding or other appropriate mixing process additional materials such as graphite/carbon fibers and/or ceramic/metallic additives, and in order to replicate human joint cartilage. While no specific dimensions are provided, it is generally understood that the mat 20 exhibits a suitable length, width and thickness (overall 3D configuration) such that it adequately replicates a replacement joint structure such as associated with a hip, knee, elbow, ankle or the like.

Fluid lubricant is generally shown at 22 in each of the several illustrations associated with the present inventions. As will be described in further detail, the lubricant 22 includes in a first embodiment a naturally producing lubricant associated with normal joint operation, the mat 20 construction being such that is collects (such as through natural seepage or aggegration) the lubricant across its surface area and, further by virtue of the ridge and valley configuration associated with a given mat, is capable of evenly distributing the lubricant along opposite contacting surfaces with the soft plastic layers 16 and 18 of the male 12 and receiver 14 bones. As further previously described, it is also envisioned that the lubricant 22 can also include such as synthetic fluid which is either pre-loaded into an interior ballast associated with the polymeric base substrate of the mat or, additionally or alternatively, is capable of being selectively and iteratively injected through such as a needle or the like and in order to refill or replenish the lubricant holding reservoir associated with the design.

Figure 3:
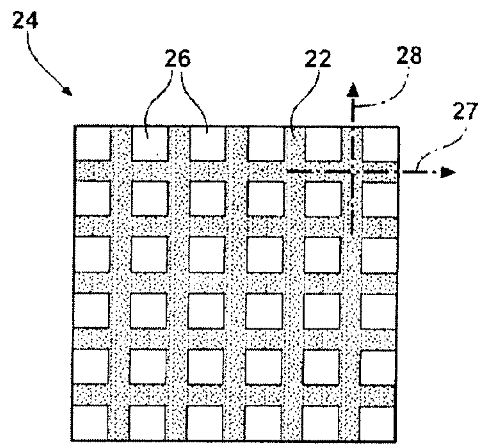
FIG. 3 is a first selected mat configuration according to one variant of the present inventions and showing a generally grid shaped pattern optimizing seepage and equal surface area distribution of either synthetic or naturalibiological generated lubricants for assisting in long-term wear and support.

Referring now to FIG. 3, a mat configuration is generally shown at 24 according to one variant of the present inventions, and showing a generally grid shaped pattern optimizing seepage and equal surface area distribution of either synthetic or natural/biological generated lubricants, again at 22, for assisting in long-term wear and support. The arrangement shown in FIG. 3 includes a plurality of individual, spaced apart and generally rectangular shaped polymeric based projections 26, between which are defined interconnected and plural x 27 and y 28 axis channels and through which the lubricant 22 is retained.

The mat construction 24 again incorporates select additives of carbon/graphite fibers, along with ceramic and/or metallic based additives (according to any of flake, granular or powder base) which are mixed or otherwise entrained into the base matrix and subsequently molded into the mat construction. In use, and consistent with each of the multiple variants described herein, the projections 26 establish contact ridges, and which support contact locations with the joint defining end surface of the opposing bone (e.g. male hardened plastic bone 12 with softened cartilage defining end surface 16), concurrent with the lubricant defined passageways 27 and 28 providing enhanced and improved frictionless and wear resistant contact support.

Figure 4:
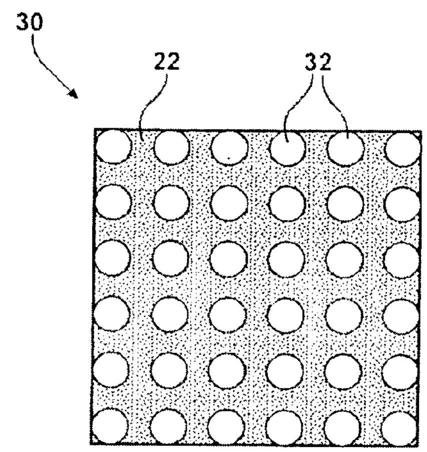
FIG. 4 is a second selected configuration characterized by such as a plurality of plastic or otherwise deformable portions which are entrained or otherwise embedded into a polymeric based and graphite and/or carbon entrained mat, and into which is further entrained a ceramic and/or metallic impregnate for increasing wear-resistant characteristics.

FIG. 4 illustrates a second selected mat configuration 30, characterized by such as a plurality of plastic or otherwise deformable portions 32 which are entrained or otherwise embedded into a graphite and/or carbon entrained and polymeric based mat, and into which is further entrained a ceramic and/or metallic impregnate for increasing wear-resistant characteristics. While somewhat modified, the x and y interconnected channels (again at 27 and 28 in FIG. 3) are again provided for in FIG. 4, with the rounded configuration of the deformable portions 32 providing a modified arcuate/curved interconnecting nature of the distributed lubricant/fluidic medium 22.

Figure 5:
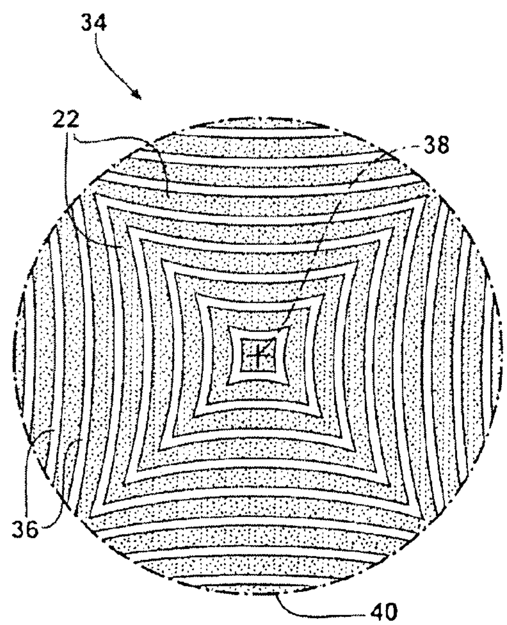
FIG. 5 is a yet further mat configuration exhibiting properties similar to that in each of FIGS. 3 and 4.

FIG. 5 illustrates a yet further mat configuration 34, again exhibiting properties similar to that in each of FIGS. 3 and 4. Of note, the plasticized substrate is reconfigured as elongated and concentric ridges, see at 36, and such as are arranged with multiple (four as shown) interconnecting sides. The lubricant 22 fills a plurality of likewise four-sided and individual valleys established between each interconnected and multi-sided ridge, and along opposite sides of each elongated ridge, concentrically from a center-most location 38 to a generally outermost radial location 40. If desired, it is also understood that the valleys can be interconnected in certain instances, such as by sectioning portions of the ridges, and to thereby improved equalized lubricant fluid distribution.

Figure 6:
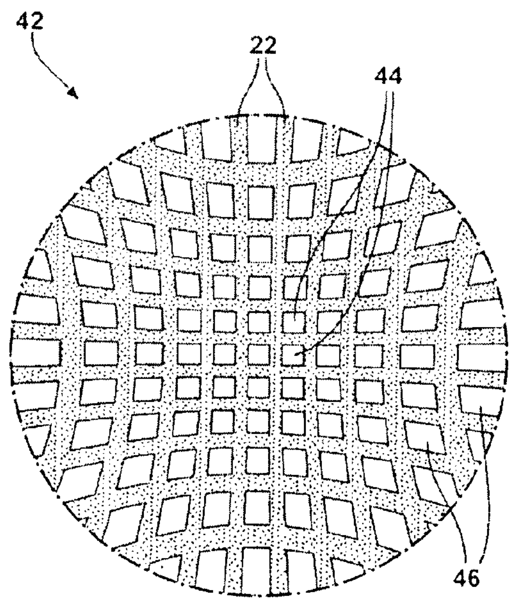
FIG. 6 is an additional mat configuration again referencing the alternate designs of FIGS. 3-5.

Referring to FIG. 6, an additional mat configuration 42 complements the individual and alternate designs of each of FIGS. 3-5. The configuration 42 is similar in respects to that shown in FIG. 3 and includes a plurality of modified rectangular (e.g. such as a hybrid trapezoidal/parallelogram) shaped projections (and as compared to those shown at 26 in FIG. 3). The configuration of FIG. 6 is such that the individual projections are arranged according to a desired size and spacing (separation), in one application with smaller sized projections 44 approximate the center location and progressively larger sized projections 46 established towards the outer perimeter locations of the mat 42. Depending upon the sizing of the radially spaced projections, either consistent or progressively larger fluid/lubricant defining and intercommunicating passageways 22 can established towards the outer perimeter locations of the mat 42.

Figure 7:
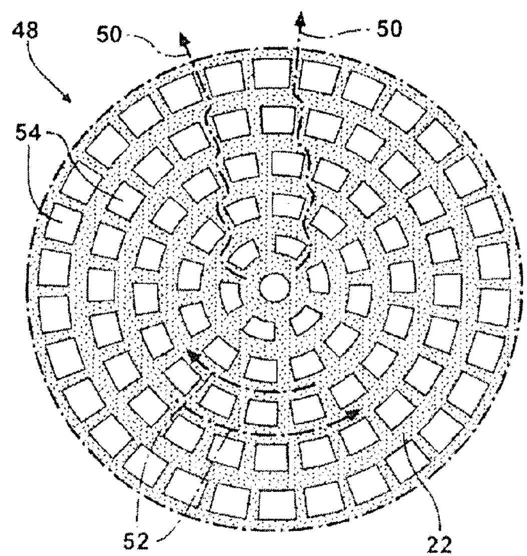
FIG. 7 is an end surface illustration of another mat configuration and employing a plurality of combined radially and concentrically configured fluid pathways.

Referring now to FIG. 7, an end surface illustration is shown at 48 of another mat configuration, this employing a plurality of combined radially 50 and concentrically 52 configured fluid pathways. As with previous embodiments, multiple pluralities of multi (four) sided projections 54 can be provided, and as shown can exhibit varying sizes with a modified trapezoidal configuration when compared to that shown at 44 and 46 in FIG. 6. The individually defined projections 54 associated with the matrix composition of FIG. 7 each further exhibit arcuate inner and outer edge surfaces, these establishing the concentric fluid pathways 52, it further being understood that a base surface supports and interconnects all of the projections 54, and upon which the interconnected fluid passageways 52 and 54 are defined.

Figure 8:
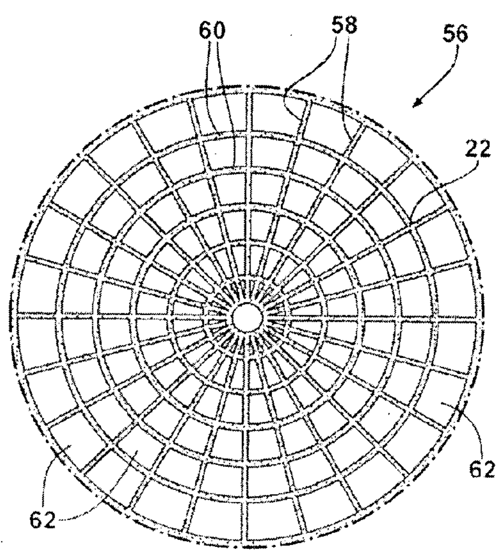
FIG. 8 is a further mat configuration exhibiting aspects alternate to that shown in FIG. 7.

FIG. 8 is a further mat configuration 56 exhibiting aspects alternate to that shown in FIG. 7 and in particular showing a more generally radial/linear defined arrangement of fluid pathways 58 in combination with concentric interconnected passageways 60. A plurality of base supported and spaced apart/projecting portions 62 are provided, these each exhibiting a generally trapezium or trapezoidal shape and in order to create another uniquely configured and passageway supporting network for the associated lubricant.

Figure 9:
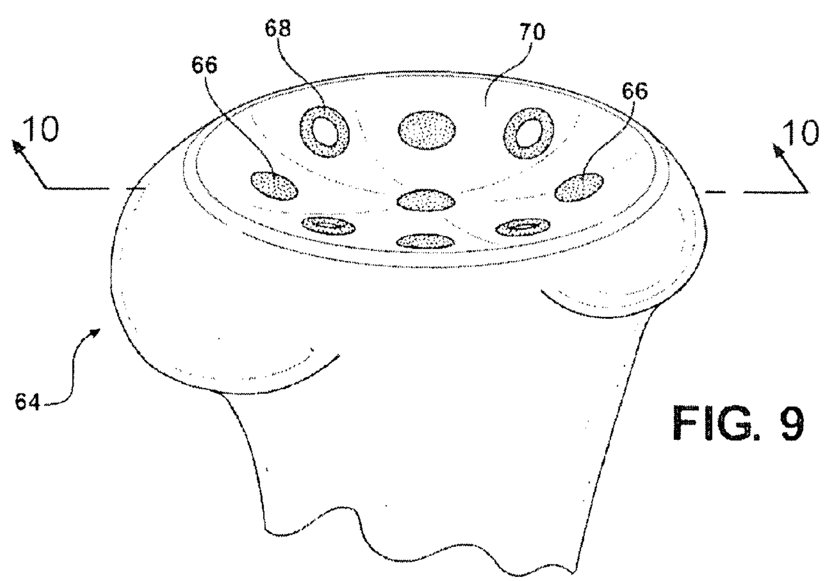
FIG. 9 is a perspective end view of such as a receiver bone end surface of a selected bone and including a plurality of fluid filled pockets/cavities according to a variety of different configurations.

FIG. 9 is a perspective end view 64 of a modified receiver bone end surface, and depicting a plurality of fluid filled pockets/cavities according to a variety of different configurations, this substituting directly for the intermediately supported mat of the several preceding variants. In particular, the pocket defined cavities may include rounded or arcuate shaped cavities, see at 66, as well as doughnut shaped cavities, at 68, all for the purpose of establishing a frictionless lubricated and wear resistant surface all across the inner recessed surface profile 70 for the defined joint.

Figure 10:
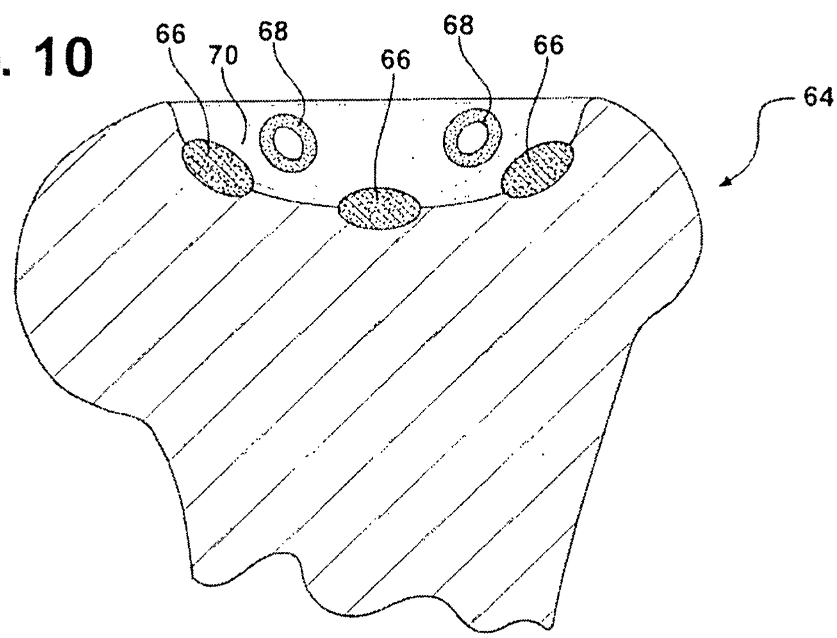
FIG. 10 is cross sectional side view along line 10-10 of FIG. 9 and showing from another angle the fluid retaining pockets of FIG. 9.

FIG. 10 is cross sectional side view along line 10-10 of FIG. 9 and further showing, from another angle, the fluid retaining pockets of FIG. 9. In particular, and although the receiving, and recessed, pocket surface 70 of the bone 64 is illustrated in a less inwardly recessed pronounced fashion, it is understood that such a surface can also exhibit an inner/arcuately defined, and substantially spherical, configuration such as is shown in FIGS. 1 and 2.

Figure 11:
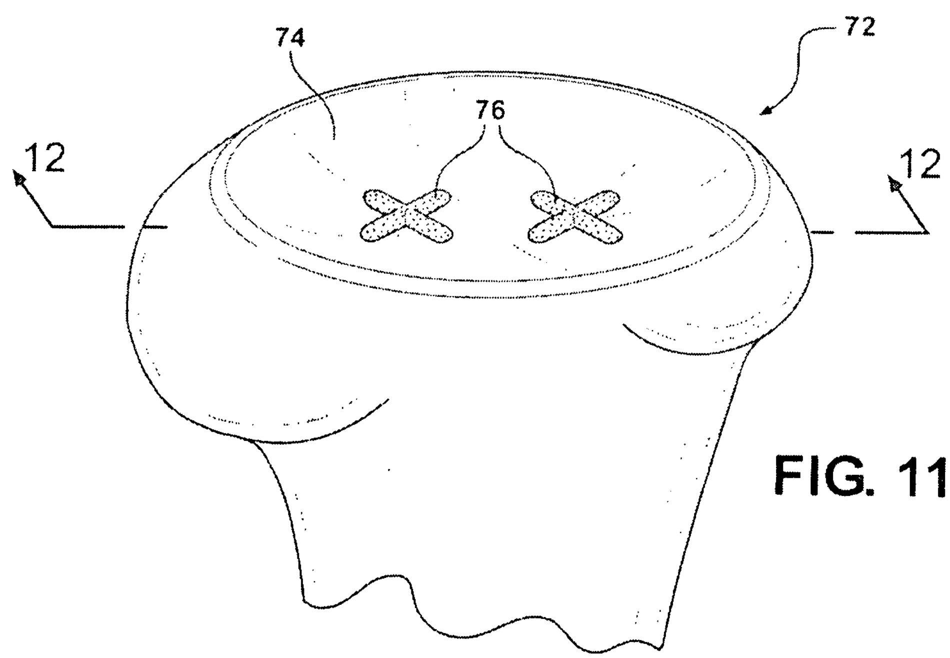
FIG. 11 is a perspective end view of another variation of receiver bone end surface exhibiting cross-shaped fluid retaining pockets.
Figure 12:
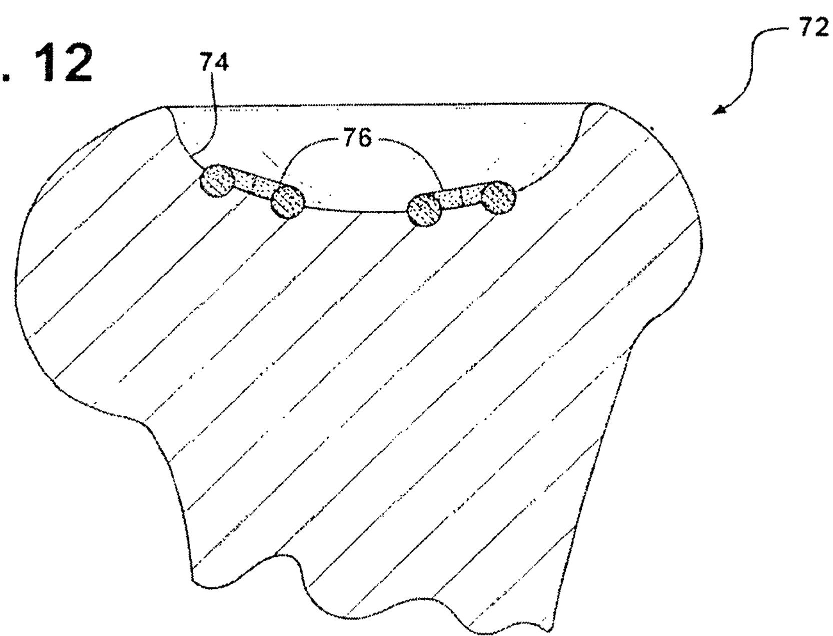
FIG. 12 is a cross sectional side view along line 12-12 of FIG. 11 and showing from another angle the fluid retaining pockets of FIG. 11.

Referencing finally FIGS. 11 and 12, perspective end facing and cross sectional side views are presented of another variation of receiver bone 72, with an associated (and again inwardly recessed) end surface 74 exhibiting alternatively configured and cross-shaped fluid retaining pockets 76. The configuration of the pockets 76 can be such as to improve localized concentration of lubricant, in cooperation with the sizing, spacing and placement of the pockets across the surface of the receiver bone to which it is affixed.

Having described my invention, other and additional preferred embodiments will become apparent to those skilled in the art to which it pertains, without deviating from the scope of the appended claims.

I claim:

1. An artificial joint associated with an implant, a pair of three dimensional and structurally extending bones including a male bone and a female bone, each defining a contoured and opposing end face, which collectively defines a joint location, said joint comprising:

a first softened plasticized layer adapted to being applied to a convex end face of the male bone;

a second softened plasticized layer adapted to being applied to an opposing and concave end face of the female bone and, upon seating the convex end face of the male bone, coacting in an articulating fashion;

a polymeric based mat exhibiting a selected length, width and thickness and which is flexibly secured upon a selected one of said convex or concave shaped plasticized layers, said mat filling a three dimensional space associated with the joint location between said first and second plasticized layers and so that an exposed surface of said mat articulates relative to the other selected one of said plasticized layers, said exposed surface of said mat having a plurality of projecting contact locations with said other selected plasticized layer, a network of intercommunicating and lubricant retaining channels extending around said projecting contact locations, said network of channels including a first plurality of radially outward extending passageways intersecting a second plurality of concentrically arranged passageways for receiving, supporting, and distributing the lubricant evenly across a surface area associated with said articulating layer in friction reducing fashion; and a hardened plastic terminating in each of said first and second softened layers, a plurality of ridges formed with said mat defining contact locations for said other softened plastic layer associated with the other of the bones.

2. The invention as described in claim 1, said mat further comprising a first additive selected from at least one of a carbon and a graphite, and a second additive selected from at least one of a ceramic and a metal for providing said flexible and polymeric based mat with enhanced wear resistant properties.

3. The invention as described in claim 1, said bones each having a specified shape and size and establishing a joint selected from a group including at least one of upper/lower knee joint and an outer/inner ball and socket joint.

4. The invention as described in claim 1, said plasticized layer having a specified shape and size and further comprising an antimicrobial plastic.

* * * * *